United States Patent [19]

Coultas

[11] Patent Number: 5,197,595
[45] Date of Patent: Mar. 30, 1993

[54] FLEXIBLE SELF-REGULATING HEATING PAD FOR COMPRESSED GAS CYLINDERS

[76] Inventor: Jamie A. Coultas, 7211 Las Brisas, Houston, Tex. 77083

[21] Appl. No.: 578,745

[22] Filed: Sep. 6, 1990

[51] Int. Cl.$^5$ .............................................. H05B 1/00
[52] U.S. Cl. ..................................... 206/0.6; 219/529; 219/535
[58] Field of Search ...................... 206/0.6, 0.7; 220/3, 220/3.1; 219/521, 526, 527, 528, 529, 534, 535, 536, 538, 549

[56] References Cited

U.S. PATENT DOCUMENTS

| | | | |
|---|---|---|---|
| 4,072,848 | 2/1978 | Johnson et al. | 219/535 |
| 4,281,238 | 7/1981 | Noma et al. | 219/535 |
| 4,633,061 | 12/1986 | Arikawa | 219/202 |
| 4,695,703 | 9/1987 | Williams | 219/212 |
| 4,695,712 | 9/1987 | Busch | 219/535 |
| 4,743,321 | 5/1988 | Soni et al. | 219/535 |
| 4,810,859 | 3/1989 | Anabtawi et al. | 219/535 |
| 4,833,299 | 5/1989 | Estes | 219/311 |
| 4,891,501 | 1/1990 | Lipton | 219/528 |

FOREIGN PATENT DOCUMENTS

| | | | |
|---|---|---|---|
| 0032850 | 3/1979 | Japan | 219/535 |
| 2181029 | 4/1987 | United Kingdom | 219/528 |

*Primary Examiner*—Jimmy G. Foster

[57] ABSTRACT

A flexible self-regulating heating pad apparatus (10) in combination with a compressed gas cylinder (50); wherein, the flexible self-regulating heating pad apparatus )10) consists of a flexible self-regulating heating unit (34); an insulation unit (36); a jacketing unit (38); and a releasable attachment system (40) for installing the flexible self-regulating heating pad apparatus (10) in a circumferential fashion around the compressed gas cylinder (50) to increase the temperature and concurrently the pressure of the contents (54) of the cylinder (50).

3 Claims, 4 Drawing Sheets

FLEXIBLE SELF-REGULATING HEATING PAD FOR COMPRESSED GAS CYLINDERS

TECHNICAL FIELD

The present invention relates generally to electric heating units, and in particular to a self-regulating flexible heating unit for the circumferential heating of compressed gas cylinders.

BACKGROUND OF THE INVENTION

Compressed gas cylinders incorporate one or more fusible plugs embedded in the wall of the cylinder, or cylinder outlet valve, to prevent overpressurization of the cylinder due to overheating. When excessive heat is applied to the compressed gas cylinder, the fusible plug(s) melt before overpressurization can occur and cause the cylinder to rupture. Should a fusible plug melt, or a compressed gas cylinder rupture, potentially harmful gas and liquid in the cylinder will be released to the atmosphere.

As can be seen by reference to U.S. Pat. Nos.: 4,633,061; 4,695,703; 4,695,712; and 4,833,299, the prior art is replete with myriad and diverse patented constructions which provide flexible heating pads.

While the prior art constructions are adequate for the purpose and function for which they were specifically designed, they fall far short of providing the safety and economy of a flexible self-regulating heating pad that is suited to conform to and be removeable from a compressed gas cylinder.

For instance, in the U.S. Pat. No. 4,833,299 of Estes (1989), there is described a flexible heating wrap which includes a plurality of heating elements controlled by individual temperature responsive control devices which are used to regulate the quantity of heat output by the heating wrap.

This present invention utilizes the thermal characteristics of a self-regulating heating element in combination with the physical dimensions of the heating pad, and the heat retaining characteristics of the insulating material to regulate the quantity of heat output to a cylinder. The advantages of using a self-regulating heating element without other separate temperature responsive control devices include safety, as the heating pad can never exceed the melt temperature of the fusible plug(s) in the compressed gas cylinder or cylinder outlet valve; and economy of operation, by virtue of the electrical and thermal operating characteristics of the self-regulating heating element.

BRIEF SUMMARY OF THE INVENTION

The present invention involves, in general, a flexible heating pad construction designed to transfer heat from the heating pad construction to a specific article such as a sulfur dioxide gas cylinder. The heating construction of this invention includes in general a flexible self-regulating heating unit, an insulation unit, and a jacketing unit which are used in specific combination to maintain the pressure of the particular gas in a cylinder within a predetermined range, by raising the temperature of the cylinder, while concurrently eliminating the possibility of overheating the cylinder.

The heating unit that forms the basis of the present invention includes in general a flexible self-regulating heating element with an auto-therming temperature below the melt temperature of the fusible plug(s) in the compressed gas cylinder, and a power supply element.

The insulation unit includes in general a flexible insulation member; wherein, the insulation member is disposed so that the majority of the heat generated by the heating unit will be conducted directly to the body of the compressed gas cylinder.

The jacketing unit includes in general: a cover member for the insulation unit; a cover member for the heating unit; and a restraining system; wherein, the cover member for the insulation unit forms an envelope which encloses the insulation unit; and the cover member for the insulation unit and the cover member for the heating unit are attached to form an annulus which encloses the heating unit.

The restraining system includes in general, cooperating hook and loop fastening elements or cinch straps with ring type closures, or both cooperating hook and loop fastening elements and cinch straps with ring type closures; wherein, the fastening elements are attached at the circumferential ends of the jacketing units in a well recognized manner.

Briefly stated, the aforementioned arrangement provides a flexible heating pad construction which may be releasably attached and closely conformed around a compressed gas cylinder; wherein the compressed gas cylinder is efficiently heated by this construction, without the possibility of overheating the cylinder.

BRIEF DESCRIPTION OF THE DRAWINGS

The above and other objects, advantages, and novel features of the invention will become apparent from the detailed description of the best mode for carrying out the preferred embodiments of this invention which follows, particularly when considered in conjunction with the accompanying drawings, wherein.

DESCRIPTION OF THE PREFERRED EMBODIMENTS

Figure 1:
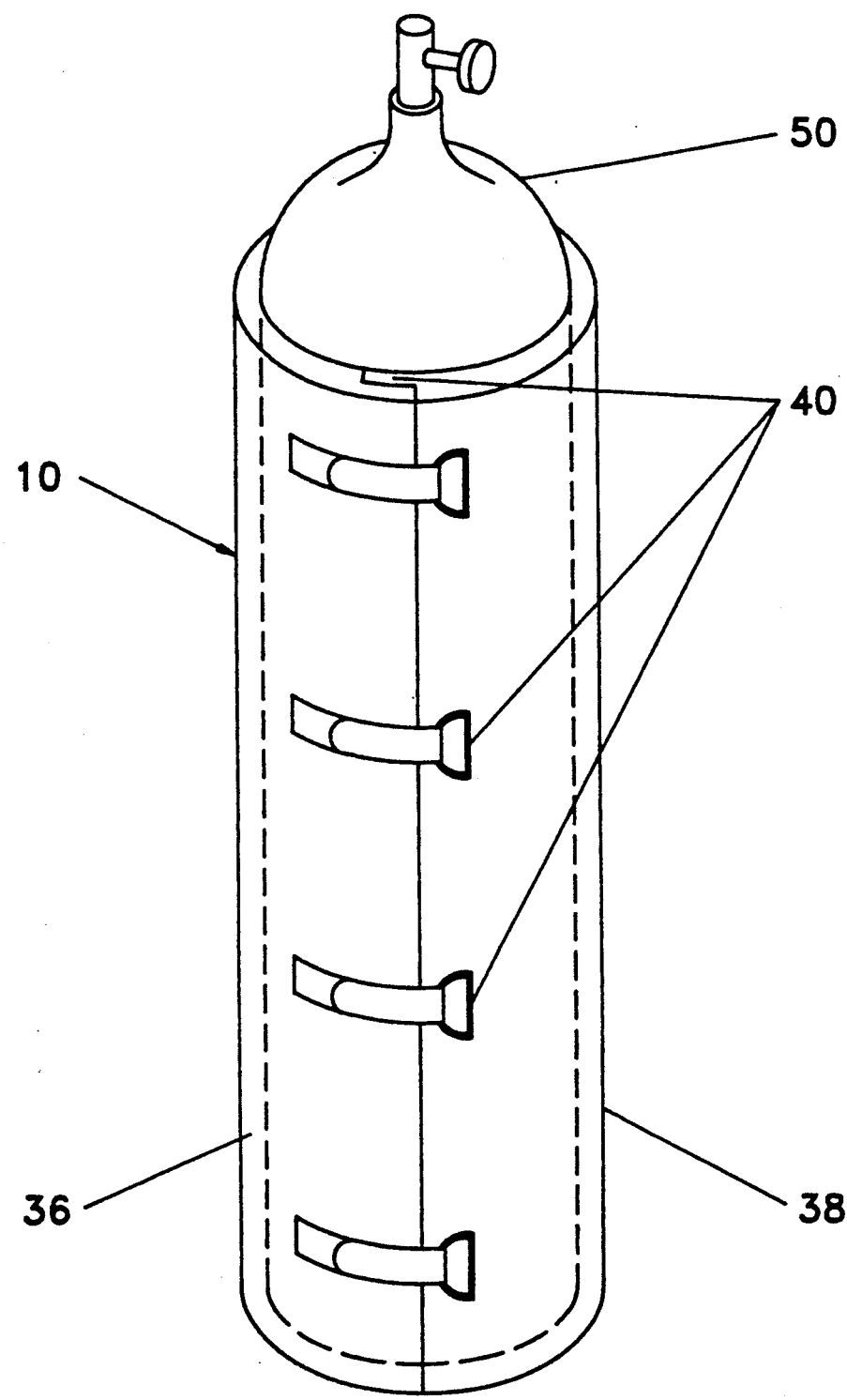
FIG. 1 is a perspective view of one embodiment of the apparatus installed on a chlorine cylinder.

As can be seen by reference to the drawings and particular to FIG. 1, the flexible heating pad apparatus that forms the basis of the present invention was specifically developed for use with a compressed gas cylinder (50); and, is designated generally by the number (10). The heating pad apparatus (10) in general consists of a flexible self-regulating heating unit (34) an insulation unit (36) a jacketing unit (38) and a releasable system of attachement to the cylinder (40).

As shown in FIGS. 1 through 4, the heating pad apparatus (10) has a generally flat rectangular shape; wherein, the heating pad apparatus is dimensioned to surround and substantially cover the compressed gas cylinder (50). The heating pad apparatus (10) will be in intimate contact with the compressed gas cylinder (50), and the heat generated by the heating pad apparatus (10) will be transferred through the wall of the pressurized gas cylinder (52) and maintain the pressure of the contents of the cylinder (54) within the prescribed pressure limits for the specific contents of the cylinder (50).

Figure 3:
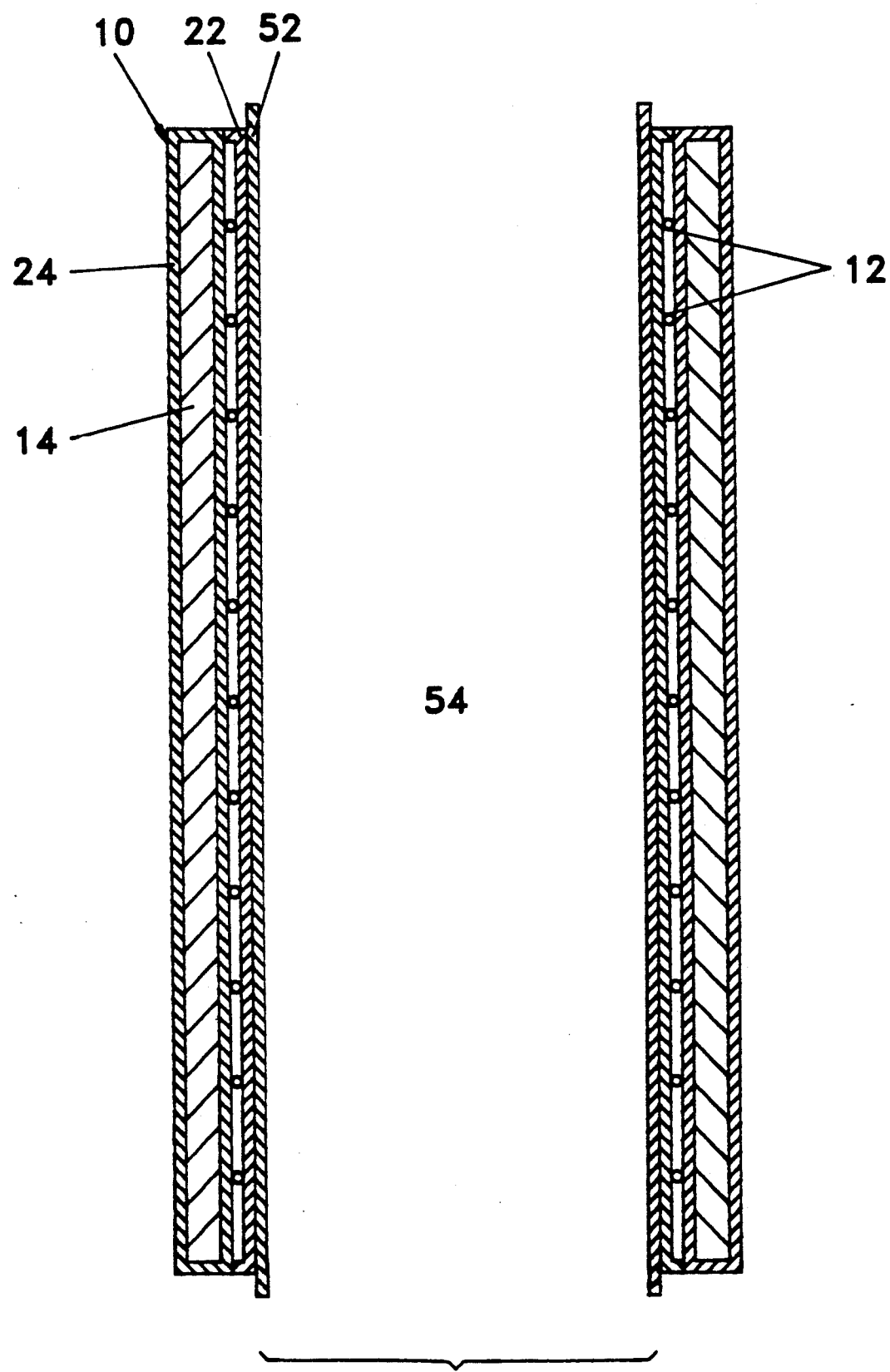
FIG. 3 is a cross-sectional view of the apparatus and a chlorine cylinder on which it is installed taken through line 4—4 of FIG. 1.
Figure 4:
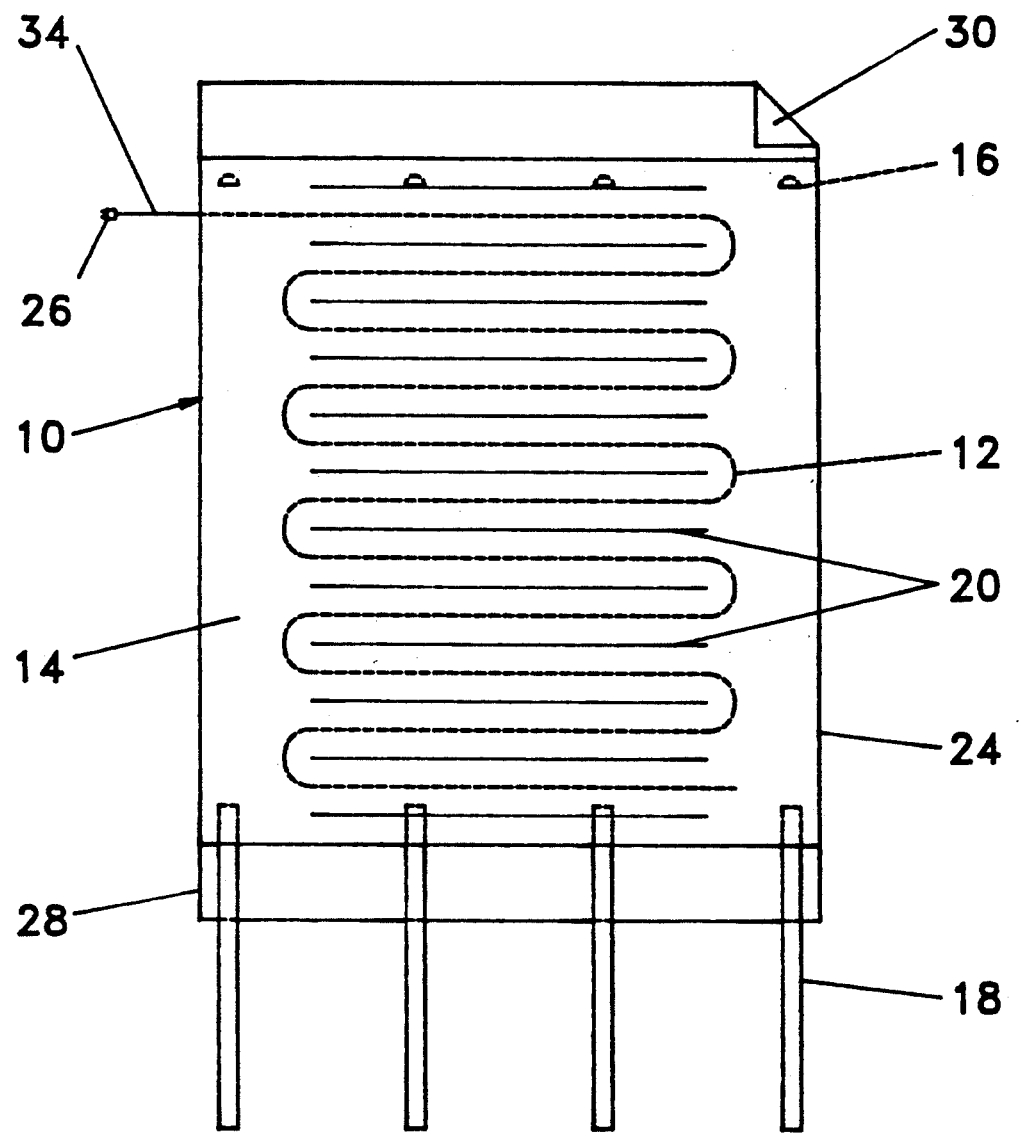
FIG. 4 is a top plan view of the heating element within the embodiment of the apparatus shown in FIG. 1.

As can best be appreciated by reference to FIGS. 3 and 4, the flexible self-regulating heating unit (34) includes a flexible self-regulating heating element (12) and an electrical input and output member in the form of an electrical plug (26).

The insulation unit (36) includes in general a generally rectangular flexible mat (14) of insulation material.

Figure 2:
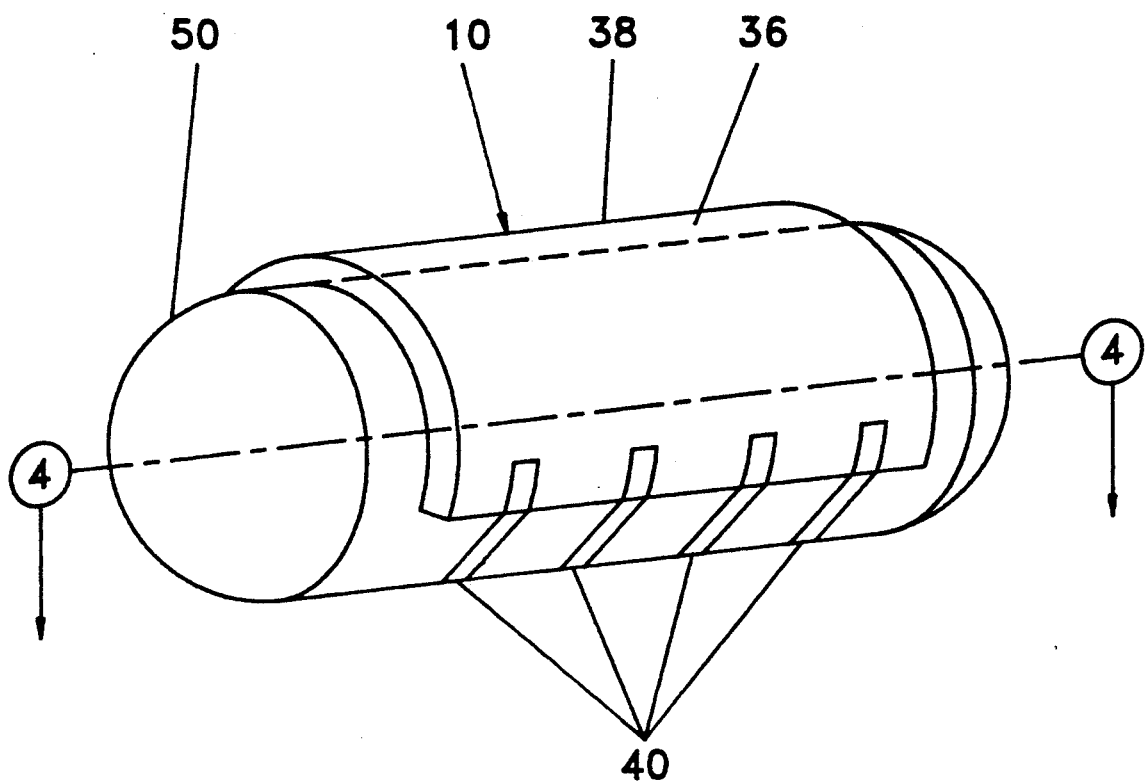
FIG. 2 is a perspective view of another embodiment of the apparatus installed on a sulfur dioxide cylinder.

The jacketing unit (38) includes generally a fabric envelope (24) that surrounds the flexible insulation unit (36) and a fabric cover (22) that encloses the flexible self-regulating heating unit (34); wherein the ends of the jacketing unit are provided with the releasable means (40) of attaching the jacketing unit intimately around a substantial portion of the circumference of the pressurized gas cylinder (50) as shown in FIGS. 1 and 2.

As can best be appreciated by reference to FIGS. 1 and 2, the releasable system (40) of attachment includes hook (28) and loop (30) fasteners which are located on opposite sides of each end of the jacketing unit, or cinch straps (18) with ring type closures (16) which are located on each end of the jacketing unit, or both hook (28) and loop (30) fasteners and cinch straps (18) with ring type closures (16).

In one version of the preferred embodiment the heating pad apparatus (10) is installed on a compressed gas cylinder (50) with the releasable system (40) of attachment that includes hook (28) and loop (30) fasteners and cinch straps (18) with ring type closures (16). In this version of the preferred embodiment, the heating pad apparatus (10) would fully cover the circumference of the compressed gas cylinder (50) as shown in FIG. 1

In another version of the preferred embodiment, the heating pad apparatus (10) is installed on a compressed gas cylinder (50) with the releasable system (40) of attachment that includes cinch straps (18) with ring type closures (16). In this version of the preferred embodiment the heating pad apparatus (10) would cover a portion of the circumference of the compressed gas cylinder (50), as shown in FIG. 2.

Referring to FIG. 4 it can be seen that the self-regulating heating element (12) is held semi-captive relative to the jacketing unit (38) and the insulation unit (36) by virtue of a plurality of seams (20) that are sewn or welded at spaced locations both between and adjacent to the continuous length of the heating element (12). The seams (20) extend between the cover member (22) for the heating unit (22) and the fabric cover (22) for the heating unit and the fabric envelope (24) for the insulation unit.

The mode of operation of this invention involves attaching the heating pad apparatus (10) to a compressed gas cylinder (50) and inserting the electrical plug member (26) into an electrical outlet (not shown) to energize the self-regulating heating element (12), such that the temperature of the self-regulating heating element (12) will rise to and maintain a temperature within a predetermined value range dictated by the thermal characteristics of the self-regulating heating unit (34), the heat retaining characteristics of the insulation unit (36), and the physical size of the heating pad apparatus (10). The heat transfer between the heating pad apparatus (10) and the wall of the compressed gas cylinder (52) will raise the temperature and concurrently the pressure of the contents of the cylinder (54).

Having hereby described the subject matter of this invention it should be apparent that many substitutions, modifications, and variations of the invention are possible in light of the above teachings. It is therefore to be understood that the invention as taught and described herein is only to be limited to the extend of the breadth and scope of the appended claims.

I claim:

1. A heating pad apparatus in combination with a compressed gas cylinder; wherein, the heating pad apparatus consists of:

a flexible heating unit that consists of a flexible self-regulating heating element and an electrical input and output member; an insulation unit adjacent to one side of the flexible heating unit; wherein the insulation unit consists of a generally rectangular mat of insulation material; a housing unit consisting of a fabric envelope that surrounds the insulation unit and an attached fabric cover that encloses the flexible heating unit, and a releasable system of attachment located at opposite ends of the housing unit; whereby, the housing unit may be installed around the circumference of said compressed gas cylinder.

2. The combination of claim 1 wherein the releasable system of attachment consists of:

integral multiple cinch strap and ring type closure combinations located at opposite ends of the jacketing unit such that the jacketing unit may be installed circumferentially on a cylinder.

3. The combination of claim 1 wherein the releasable system of attachment consists of:

integral multiple cinch strap and ring type closure combinations, and cooperating hook and loop fastners located at opposite ends of the jacketing unit such that the jacketing unit may be installed circumferentially on a cylinder.

* * * * *